United States Patent [19]

Sih

[11] 4,283,575
[45] Aug. 11, 1981

[54] 2-DECARBOXY-2-HYDROXYMETHYL-19-HYDROXY-6A-CARBA-PGI$_2$ COMPOUNDS

[75] Inventor: John C. Sih, Portage, Mich.

[73] Assignee: The Upjohn Company, Kalamazoo, Mich.

[21] Appl. No.: 126,470

[22] Filed: Mar. 3, 1980

Related U.S. Application Data

[62] Division of Ser. No. 54,811, Jul. 5, 1979, Pat. No. 4,225,508.

[51] Int. Cl.$^3$ .................... C07C 49/633; C07C 35/31
[52] U.S. Cl. ..................................... 568/819; 568/374
[58] Field of Search ............................... 568/819, 374

[56] References Cited

PUBLICATIONS

Johnson et al., Prostaglandins, vol. 12, pp. 915–928, (1976).
Johnson et al., J.A.C.S., vol. 100, pp. 7690–7704, (1978).
Fried et al., Proc. Nat'l. Acad. Sci., U.S.A., vol. 74, pp. 2199–2203.
Nicolaou et al., J.C.S. Chem. Comm., 1977, pp. 331–332, (1977).
Nelson et al., J.A.C.S., vol. 99, pp. 7362–7363, (1977).
Kojima et al., Tetra Letters, p. 1978, (1977).
Kojima et al., Tetra Letters, pp. 3743–3746, (1978).
Johnson, Prostaglandins, vol. 15, pp. 737–740, (1978).

*Primary Examiner*—Howard T. Mars
*Assistant Examiner*—James H. Reamer
*Attorney, Agent, or Firm*—Robert A. Armitage

[57] ABSTRACT

The present invention provides novel 2-decarboxy-2-hydroxymethyl-19-hydroxy-6a-carba-PGI$_1$ compounds which are useful for pharmacological purposes, e.g., anti-asthmatic indications.

4 Claims, No Drawings

2-DECARBOXY-2-HYDROXYMETHYL-19-HYDROXY-6A-CARBA-PGI₂ COMPOUNDS

CROSS REFERENCE TO RELATED APPLICATION

The present invention is a divisional application of U.S. Pat. No. 054,811, filed 5 July 1979, now U.S. Pat. No. 4,225,508.

BACKGROUND OF THE INVENTION

The present invention provides novel prostacyclin analogs. Particularly, the present invention relates to prostacyclin analogs substituted at the C-19 position by hydroxy.

Particularly, the present invention relates to 2-decarboxy-2-hydroxymethyl-19-hydroxy-6a-carba-PGI₂ compounds. The novel prostacyclin analogs are useful for pharmacological purposes, e.g., as anti-asthmatic agents. The preparation and use of these compounds is incorporated here by reference from U.S. Pat. No. 4,225,508.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI₂, see R. A. Johnson, et al., Prostaglandins 15, 737–740 (1978).

SUMMARY OF THE INVENTION

The present invention particularly provides a prostacyclin-type compound of the formula

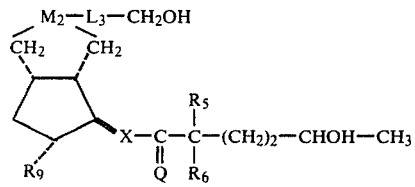

wherein $L_3$ is
(1) —$(CH_2)_n$—, wherein n is one to 5, inclusive,
(2) —$(CH_2)_p$—$CF_2$—, wherein p is 2, 3, or 4, or
(3) —$CH_2$—$CH=CH$—;
wherein $M_2$ is

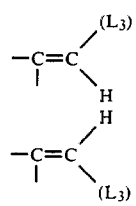

wherein Q is oxo, α-H:β-H, α-OH:β-$R_4$, or α-$R_4$:β-OH,
wherein $R_4$ is hydrogen or alkyl of one to 4 carbon atoms, inclusive,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;
wherein $R_9$ is hydrogen or hydroxyl; and
wherein X is
(1) trans—$CH=CH$—,
(2) cis—$CH=CH$—,
(3) —$C\equiv C$—, or
(4) —$CH_2CH_2$—.

DESCRIPTION OF THE PREFERRED EMBODIMENTS

The present invention particularly relates to the following compounds:
(5E)-2-Decarboxy-2-hydroxymethyl-6a-carba-9-deoxy-6,9α-epoxy-Δ⁵-19-hydroxy-PGF₁, and
(5E)-2-Decarboxy-2-hydroxymethyl-6a-carba-9-deoxy-6,9α-epoxy-Δ⁵-16,16-difluoro-19-hydroxy-PGF₁.

I claim:

1. A prostacycline-type compound of the formula

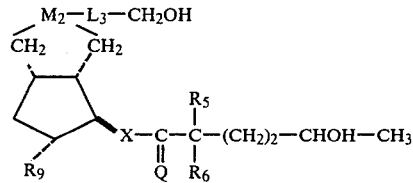

wherein $L_3$ is
(1) —$(CH_2)_n$—, wherein n is one to 5, inclusive,
(2) —$(CH_2)_p$—$CF_2$—, wherein p is 2, 3, or 4, or
(3) —$CH_2CH=CH$—;
wherein $M_2$ is

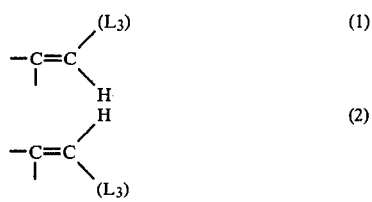

wherein Q is oxo, α-H:β-H, α-OH:β-$R_4$, or α-$R_4$:β-OH,
wherein $R_4$ is hydrogen or alkyl of one to 4 carbon atoms, inclusive,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluro;
wherein $R_9$ is hydrogen or hydroxyl; and
wherein X is
(1) trans—$CH=CH$—,
(2) cis—$CH=CH$—,
(3) —$C\equiv C$—, or
(4) —$CH_2CH_2$—.

2. A compound according to claim 1, wherein Q is α-OH:β-H, $R_9$ is hydroxy, and X is trans—$CH=CH$—.

3. (5E)-2-Decarboxy-2-hydroxymethyl-6a-carba-9-deoxy-6,9α-epoxy-Δ⁵-19-hydroxy-PGF₁, a compound according to claim 2.

4. (5E)-2-Decarboxy-2-hydroxymethyl-6a-carba-9-deoxy-6,9α-epoxy-Δ⁵-16,16-difluoro-19-hydroxy-PGF₁, a compound according to claim 2.

* * * * *